(12) United States Patent
Castro

(10) Patent No.: US 11,369,416 B2
(45) Date of Patent: Jun. 28, 2022

(54) IMPLANT FOR BONE

(71) Applicant: Blue Sky Technologies, LLC, Louisville, KY (US)

(72) Inventor: Frank Castro, Louisville, KY (US)

(73) Assignee: Blue Sky Technologies, LLC, Louisville, KY (US)

( * ) Notice: Subject to any disclaimer, the term of this patent is extended or adjusted under 35 U.S.C. 154(b) by 0 days.

(21) Appl. No.: 17/408,375

(22) Filed: Aug. 21, 2021

(65) Prior Publication Data

US 2021/0393298 A1 Dec. 23, 2021

Related U.S. Application Data

(63) Continuation-in-part of application No. PCT/US2019/054383, filed on Oct. 3, 2019.

(60) Provisional application No. 62/809,670, filed on Feb. 24, 2019.

(51) Int. Cl.
*A61B 17/70* (2006.01)
*A61B 17/16* (2006.01)

(52) U.S. Cl.
CPC .......... *A61B 17/70* (2013.01); *A61B 17/1671* (2013.01); *A61B 17/7047* (2013.01); *A61B 17/7074* (2013.01)

(58) Field of Classification Search
CPC .................................................. A61B 17/7047
USPC .................................................. 606/250–330
See application file for complete search history.

(56) References Cited

U.S. PATENT DOCUMENTS

| | | | |
|---|---|---|---|
| 3,887,186 A | 2/1975 | Matlock, Jr. | |
| 4,244,689 A | 1/1981 | Ashman | |
| 5,899,905 A * | 5/1999 | Errico | A61B 17/7032 606/256 |
| 6,159,211 A | 12/2000 | Boriani et al. | |
| 6,287,308 B1 * | 9/2001 | Betz | A61B 17/7044 606/246 |
| 6,325,805 B1 * | 12/2001 | Ogilvie | A61B 17/70 606/75 |
| 6,447,525 B2 | 9/2002 | Follmer et al. | |
| 6,743,255 B2 | 5/2004 | Ferree | |
| 6,746,484 B1 | 6/2004 | Liu et al. | |
| 8,100,972 B1 | 1/2012 | Bruffey et al. | |
| 9,636,232 B2 | 5/2017 | Neubardt | |
| 9,707,100 B2 | 7/2017 | Afferzon et al. | |
| 9,814,483 B2 | 11/2017 | Vardi | |
| 9,867,733 B2 | 1/2018 | Mohan et al. | |
| 2004/0078079 A1 | 4/2004 | Foley | |
| 2004/0133279 A1 | 7/2004 | Krueger et al. | |
| 2005/0119657 A1 * | 6/2005 | Goldsmith | A61B 17/707 606/915 |
| 2005/0119753 A1 | 6/2005 | McGahan et al. | |
| 2008/0065074 A1 * | 3/2008 | Yeung | A61B 17/7032 606/269 |
| 2009/0254125 A1 | 10/2009 | Predick | |
| 2009/0265006 A1 | 10/2009 | Seifert et al. | |

(Continued)

FOREIGN PATENT DOCUMENTS

WO WO2001085069 11/2001

*Primary Examiner* — Eduardo C Robert
*Assistant Examiner* — Tara Rose E Carter
(74) *Attorney, Agent, or Firm* — Business Patent Law, PLLC

(57) ABSTRACT

The present invention is an implant for bone. The current implant is particularly useful in spinal surgical procedures.

19 Claims, 6 Drawing Sheets

(56) References Cited

U.S. PATENT DOCUMENTS

| | | |
|---|---|---|
| 2011/0098747 A1* | 4/2011 | Donner ................ A61F 2/4611 |
| | | 606/264 |
| 2011/0264229 A1 | 10/2011 | Donner |
| 2012/0010659 A1 | 1/2012 | Angert et al. |
| 2012/0232599 A1 | 9/2012 | Schoenly et al. |
| 2013/0072991 A1* | 3/2013 | Rathbun ............ A61B 17/7041 |
| | | 606/305 |
| 2013/0150906 A1 | 6/2013 | Kerboul et al. |
| 2016/0184099 A1 | 6/2016 | Gotfried |
| 2016/0310294 A1 | 10/2016 | McConnell et al. |

* cited by examiner

IMPLANT FOR BONE

PRIORITY

Applicant claims priority to PCT/US2019/054383—Implant for Bone—, filed Oct. 3, 2019 that claims the benefit of U.S. Provisional Application No. 62/809,670—Implant for Bone—filed on Feb. 24, 2019.

BACKGROUND OF THE INVENTION

A. Field of the Invention

Among other things, the present invention is an implant for bone. The current implant is particularly suited for implantation into mammalian spinal tissues. The present implant is provided with a cutting blade or surgical cutter. Select embodiments of the current invention include surface treatments in anticipation of improving attachment of bone to the implant.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art for the current invention include: 1) U.S. Pat. No. 9,814,483—Vardi discloses a method and catheter for creating an interatrial aperture; 2) U.S. Pat. No. 3,887,186—Matlock, Jr. disclose a broadhead; 3) U.S. Pat. No. 8,199,972—Bruffey, et al. discloses a spinal cage having deployable member; 4) U.S. Pat. No. 4,244,689—Ashman discloses an endosseous plastic implant; 5) US Published Patent Application 20120232599—Schoenly, et al. discloses awl screw fixation members and related systems; 6) U.S. Pat. No. 9,636,232—Neubart discloses harvesting bone graft material for use in spinal and other bone fusion surgeries; 7) US Published Patent Application 20120010659—Angert, et al. discloses a facet fusion implant; 8) U.S. Pat. No. 6,447,525—Follmer, et al. discloses an apparatus and methods for removing material from a body lumen; 9) U.S. Pat. No. 8,070,819—Aferzon, et al. discloses an apparatus and method for anterior intervertebral spinal fixation and fusion; 10) U.S. Pat. No. 9,707,100—Duffield, et al. disclose an interbody fusion device and system for implantation; 11) U.S. Pat. No. 9,867,733—Mohan, et al. discloses a tissue adjustment implant; 12) US Published Patent Application 20040078079—Foley discloses systems and techniques for restoring and maintaining intervertebral anatomy; 13) US Published Patent Application 20090265006—Seifert, et al. discloses a lateral spinous process spacer; 14) US Published Patent Application 20160184099—Gotfried; 15) US Published Patent Application 20110264229—Donner discloses a sacroiliac joint fixation system; 16) US Published Patent Application 20130150906—Kerboul, et al. discloses a system and method for a lockable polyaxial driver tool; 17) US Published Patent Application 20090254125—Predick discloses a top loading polyaxial spine screw assembly with one step lockup; 18) WO2001085069—Lemaire, et al. discloses an anterior lumbar interbody implant; 19) U.S. Pat. No. 6,159,211—Boriani et al. discloses a stackable cage system for corpoectomy/vertebrectomy; 20) U.S. Pat. No. 6,743,255—Ferree discloses a spinal fusion cage with lordosis correction; 21) U.S. Pat. No. 6,746,484—Liu, et discloses a spinal implant; 22) US Published Patent Application 20040133279—Kruger, et al. discloses surgical implants for use as spinal spacers; 23) US Published Patent Application 2005/0119753—McGahan, et al. discloses an anterior impacted bone graft and driver instruments; and 24) 20160310294—McConnell et al. discloses a spinal fusion implant for oblique insertion.

SUMMARY OF THE INVENTION

The present invention provides a biocompatible implant for bone that can be interlocked with a device distinct from the implant. The current implant is also provided with a blade for cutting tissue. Preferred embodiments of the current fastener can also be utilized for transporting biocompatible devices/substances, such as adhesives, cameras, cannulas, fiber optics, implants, pharmaceuticals, etc. Preferred embodiments of the implant's blade are provided with an aperture. The aperture can assist tissue growth, such as bone, into and through the implant as well onto the inward surfaces of the implant. Select embodiments of the implant are provided with surface treatments in anticipation of improving attachment of bone to the implant.

With regard to spinal surgical procedures, prior art traditional fixation screws fixation stability is dependent on the healthy composition of both the cancellous bone. Those skilled in the art recognize the healthy cortical bone is from about 20 to about 100 times stronger than healthy cancellous bone. Those skilled in the art also know that increasing the screw length for osteoporotic bone rarely provides satisfactory resistance against the fixation screw from pulling-out or backing-out of bone. The blade of the current implant is shorter and wider than traditional fixation screws. Because of its novel structure and surgical insertion technique, the present implant has greater resistance against pulling-out or backing-out of osteoporotic bone. Further still, the blade's shorter length reduces the possibility of injury to nearby structures such as arteries, veins and nervous tissues. It is believed that the current invention's resistance to pull-out or back-out improves implant-construct stability, higher bone fusion rates and better postoperative clinical outcomes than prior art fixation screws.

For surgical procedures involving bone, the current implant can be inserted through a small linear aperture into the bone tissue. In one of the preferred uses of the current implant, subsequent to blade's surgical insertion into bone, the blade can be rotated up to 90 degrees relative to the plane of the surgical incision. Among other things, rotation of the blade increases resistance against pull-out or back-out of the blade from bone when compared to prior art fixation screws. It is also believed that the width of the implant's blade can contact a greater surface area of healthier cortical bone distinct from the surgically created cavity, thereby improving the possibility of successful postoperative bone fusion relative to prior art fixation screws.

Within the scope of the current invention, blades can be of symmetrical or asymmetrical configuration.

Symmetrical blades are typically preferred when the inner cortex is straight—a straight inner cortex as viewed from a lateral X-ray perspective looking at the spine. Asymmetrical blades are generally preferred when the inner cortex is sloped as seen on a lateral X-ray or sagittal CT scan). Regardless of whether symmetrical or asymmetrical, implants within the scope of the current invention require insertion and subsequent rotation of the blade of up to 90 degrees relative to the plane of the surgical incision.

In use, any surgical connecting rods will generally be parallel to the blades. In a first example for a laminectomy and fusion procedure, connecting rods and the present implant's blades will be generally vertical. In a second example for a laminoplasty procedure, the connecting rods and current implant's blades will be horizontal extending from the right side of the spinal elements to the left side spinal elements. The surgical incision will be up to 90 degrees offset from the final orientation of the implant's blade.

Various asymmetrical blade configurations are typically preferred when the surgical insertion corridor is not cylindrical. By way of illustration, when the current device is implanted into the posterior cervical facets, the blade is initially inserted through the posterior cortex perpendicular to the axis of the spinal cord. After insertion, the blade is rotated up to 90 degrees to be parallel to the axis of the spinal cord. It is believed that the asymmetrical blade allows for a greater surface area contact of the posterior cortex.

An aspect of the present invention is to provide an implant with a cutting blade.

Still another aspect of the present invention is to provide an implant with a blade that can be rotated up to 90 degrees relative to the surgical incision.

It is still another aspect of the present invention to provide an implant that improves resistance to pull-out or back-out and improves implant-construct stability, higher bone fusion rates and better postoperative clinical outcomes than prior art fixation screws.

Yet still another aspect of the present invention is to provide an implant with greater resistance against pulling-out or backing-out of osteoporotic bone that current fixation screws.

Still another aspect of the present invention is to provide an implant adapted for connection with a device distinct from the implant.

Yet another aspect of the present invention is to provide an implant with a conduit for transporting biocompatible devices/substances or chemotherapeutic agents.

It is still another aspect of the present invention to provide an implant with a blade having an aperture therein.

Yet still another aspect of the present invention is to provide an implant adaptable for use in the cervical region of the spine.

Still another aspect of the present invention is to provide an implant with a surgical cutter including a common bend.

It is still another aspect of the present invention to provide an implant adapted to cut in a forward, a clockwise or a counterclockwise direction.

Yet another aspect of the present invention is to provide an implant first and second segments where each segment has different slopes.

A preferred embodiment of the current invention can be described as an implant (320) for bone adapted for interconnection with a device distinct from the implant (320); the implant (320) comprising: a) a shaft (240) comprising a first end (242) and a second end (244) opposite the first end (242); the shaft (240) including a longitudinal axis (X-X) therein and extending away from the first end (242) and the second end (244); and b) a clip (400) comprising: i) a first arm (410) connected to first end (242) of shaft (240); the first arm (410) adapted to range from perpendicular to oblique with respect to the longitudinal axis (X-X); ii) a bridge (420) connecting a first end (412) of the first arm (410) to a first end (442) of a second arm (440); the second arm (440) adapted to range from perpendicular to oblique with respect to the longitudinal axis (X-X), wherein a second end (414) of first arm (410) and a second end (444) of the second arm (440) are biased toward each other; and iii) a blade (450) positioned proximate the second end (444) of the second arm (440).

Another preferred embodiment of the current invention can be described as an implant (500) for bone adapted for interconnection with a device distinct from the implant (500); the implant (500) comprising: a) a shaft (240) comprising a first end (242) and a second end (244) opposite the first end (242); the shaft (240) including a longitudinal axis (X-X); b) the first end (242) of the shaft (240) attached proximate a first end (512) of a cutting member (510); c) a second end (514) of the cutting member (510) opposite from the first end (512) and a blade (540) positioned proximate the second end (514) of the cutting member (510); d) an appendage (550) positioned about the shaft (240) and between the first end (242) and the second end (244) of the shaft (240); the appendage (550) parallel to the cutting member (510); e) a connector (570) connected to the shaft (240) and the appendage (550) such that the appendage (550) is rotatable about the shaft (240) at angles perpendicular to the longitudinal axis (X-X); and f) a lock (572) preventing rotation of the appendage (550).

It is the novel and unique interaction of these simple elements which creates the apparatus and methods, within the ambit of the present invention. Descriptions of preferred embodiments of the invention follow. However, it is to be understood that the best mode descriptions do not limit the scope of the present invention.

DESCRIPTION OF THE PREFERRED EMBODIMENTS

Figure 1:
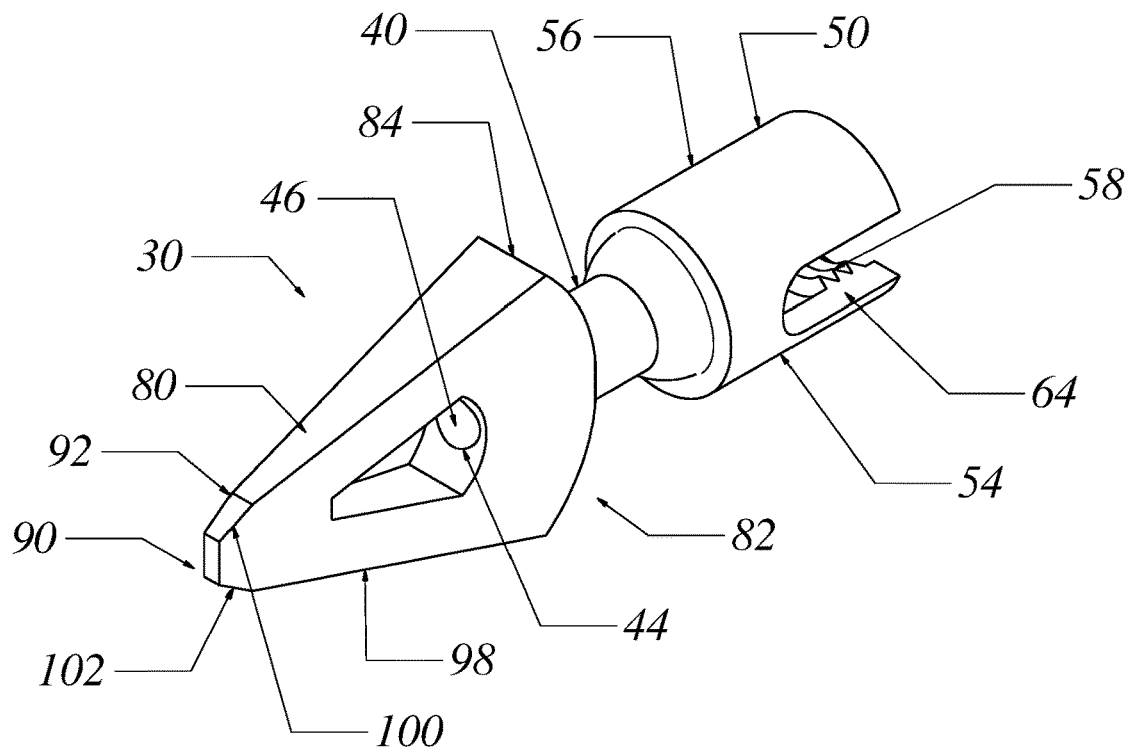
FIG. 1 is a perspective of a first preferred embodiment of the implant.

Although the disclosure hereof is detailed to enable those skilled in the art to practice the invention, the embodiments published herein merely exemplify the present invention.

In the most general sense, the present invention is an implant for bone where the implant is adapted for connection with a device distinct from the implant. Among other things, the current invention can be adapted for use with vertebra or other bone tissues. The present implant is particularly adapted for use in the cervical region of the spine. The current invention can be provided with a conduit for transporting biocompatible devices/substances or chemotherapeutic agents, such as adhesives, cameras, cannulas, fiber optics, implants, pharmaceuticals, etc. Dispersion of adhesives from the windows or openings of the implant before closing the surgical wound, reduces the risk of the fastener backing out of the wound prior to the fastener fully interlocking with tissue overgrowth. Polymethymethacrylate is an adhesive particularly well suited for use with the current fastener.

Preferred embodiments of the present invention are manufactured of titanium alloys, stainless steel, non-resorbable polymers or any other composition acceptable in the art. Within the scope of the present invention, it has advantageously been discovered that cylindrical shafts (40) can have lengths from about 2 to about 10 millimeters; polyaxial heads (50) can have lengths of from about 5 millimeters to about 25 millimeters; sockets (54) of polyaxial heads (50) can have depths from about 3 millimeters to about 23 millimeters, diameters from about 4 millimeters to about 20 millimeters, lateral openings widths (62, 64) from about 3 millimeters to about 10 millimeters; and blades (80, 120) can have lengths of from about 3 millimeters to about 12 millimeters, widths of from about 4 millimeters to about 10 millimeters and heights of from about 0.2 millimeters to about 4 millimeters.

Figure 2:
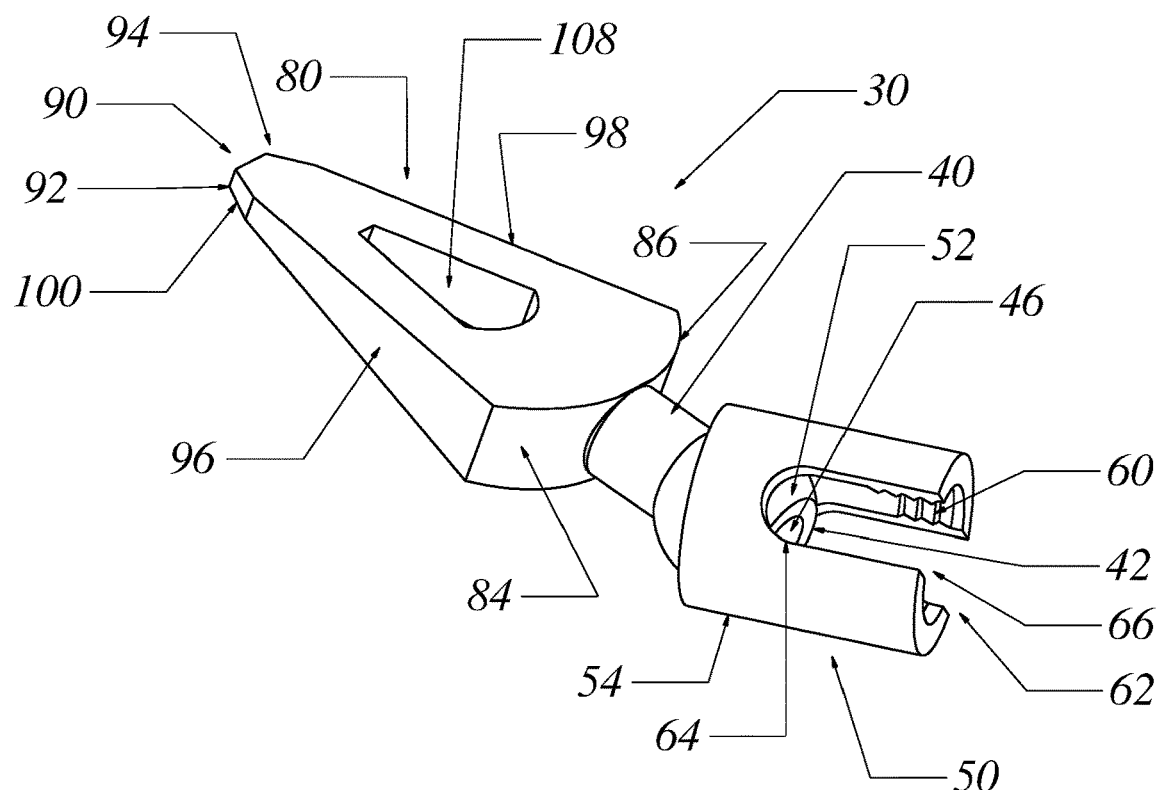
FIG. 2 is a perspective of a first preferred embodiment of the implant.

FIGS. 1 and 2 are perspectives of a first preferred embodiment of implant (30). Within the scope of the current invention, implant (30) can be interconnected with a device distinct from the implant. It has been discovered that implant (30) is useful for spinal surgeries, and, in particular, surgeries for the cervical region of the spine.

Among other things, the preferred embodiment of implant (30), enabled in FIGS. 1 and 2, includes cylindrical shaft (40), polyaxial head (50) and blade (80). Cylindrical shaft (40) includes first end (42), second end (44) and inner cavity (46) extending through first end (42) and second end (44).

Polyaxial head (50) of implant (30) is adapted for connection with a device (not shown) distinct from implant (30). Examples of devices connectable to polyaxial head (40) include but are not limited to: rods, bars, cross-links, screws and locking nuts. Polyaxial head (50) is provided with spheroid (52) connected to first end (42) of cylindrical shaft (40) and socket (54) connected to spheroid (52). Prior to surgical fixation, the combination of spheroid (52) and socket (54) allows polyaxial head (50) to be moved in a multitude of axes relative to the inner cavity (46) of cylindrical shaft (40). Socket (54) is provided with an outward housing (56) and inward receptacle (58) including one or more threads (60). Selected preferred embodiments of housing (56) can be provided with openings (62, 64, 66) adapted to receive one or more devices distinct from implant (30).

Arcuate side (82) of blade (80) is connected with second side (44) of cylindrical shaft (40). Arcuate side (82) of blade (80) is of a dimension wider than the diameter of cylindrical shaft (40). Arcuate side (82) includes first wing (84) and second wing (86) where each wing (84, 86) extends away from the longitudinal axis of cylindrical shaft (40). As shown in FIGS. 1 and 2, each wing (84, 86) is arched away from first end (42) of cylindrical shaft (40).

Straight side (90) of blade (80) is of lesser length than arcuate side (82) and positioned opposite from arcuate side (82). Straight side (90) includes first end (92) and second end (94). First converging edge (96) connected to first wing (84) and second converging edge (98) connected second wing (86) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial, osteogenic or chemotherapeutic substances into the surgically created cavity.

Figure 3:
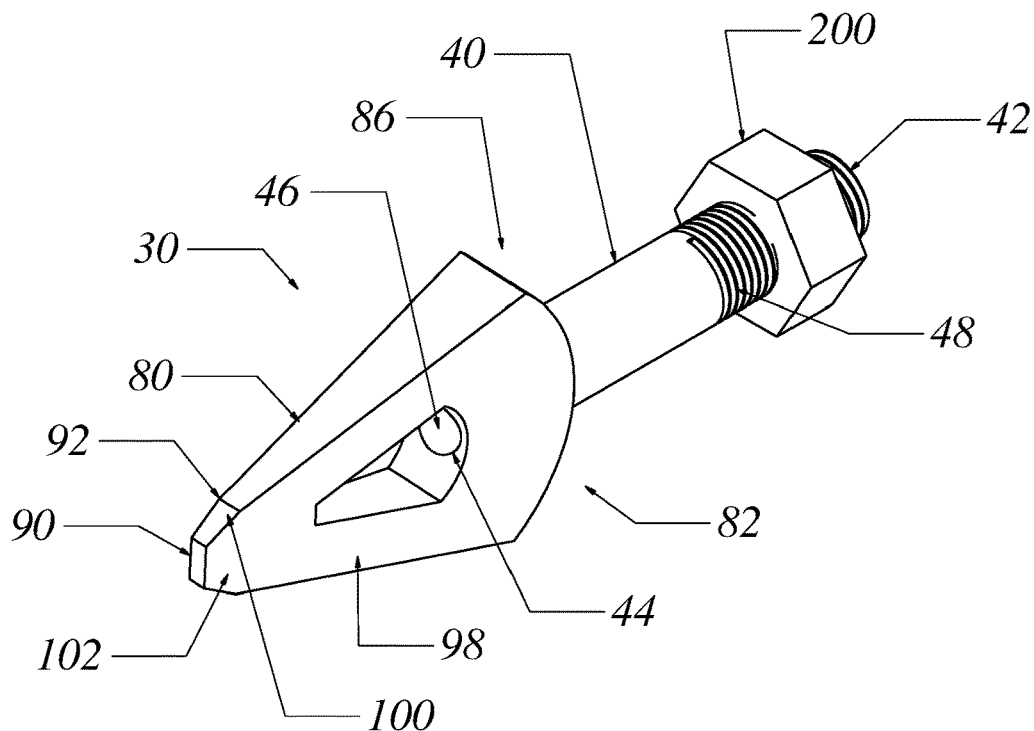
FIG. 3 is a perspective of a second preferred embodiment of the implant.
Figure 4:
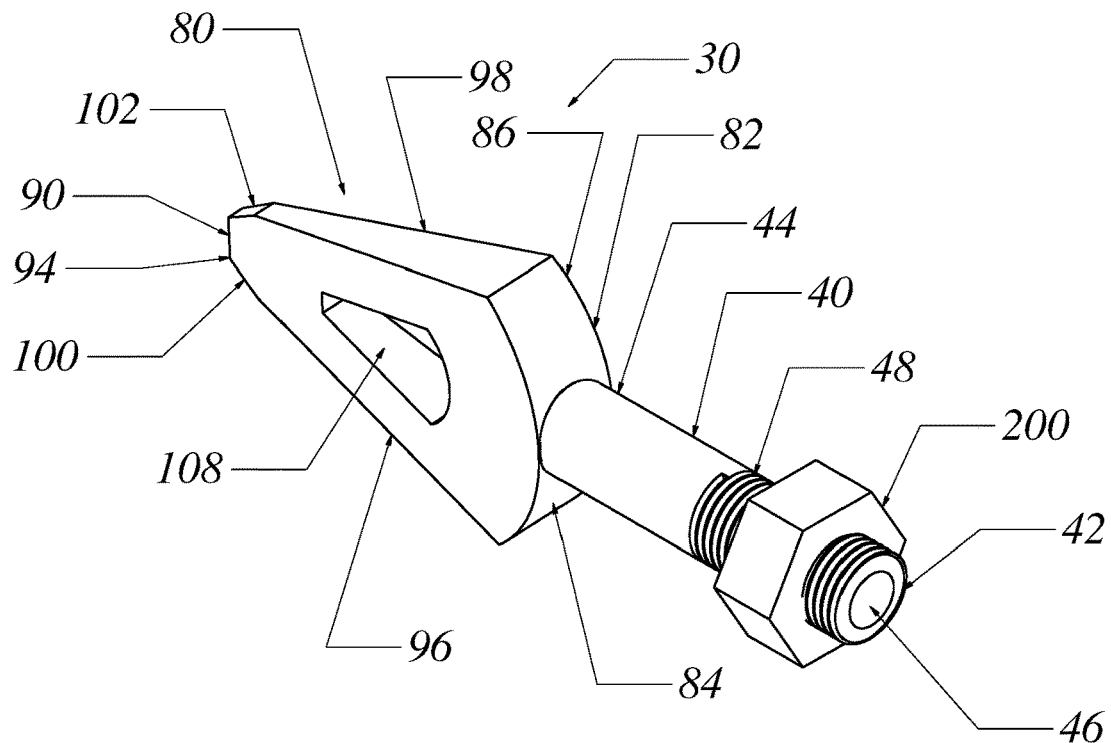
FIG. 4 is a perspective of a second preferred embodiment of the implant.

FIGS. 3 and 4 are perspectives of a second preferred embodiment of implant (30). Within the scope of the current invention, implant (30) can be interconnected with a device distinct from the implant, such as a nut (200) or other device (not shown) for coupling with implant (30). It has been discovered that implant (30) is useful for spinal surgeries, and, in particular, surgeries for the cervical region of the spine.

Among other things, the preferred embodiment of implant (30), enabled in FIGS. 3 and 4, includes cylindrical shaft (40) and blade (80). Cylindrical shaft (40) includes first end (42), second end (44) and inner cavity (46) extending through first end (42) and second end (44). First end (42) of cylindrical shaft (40) is provided with thread (48) that can be utilized to connect implant (30) to a device distinct from implant (30). Thread (48) runs about at least a portion of the outward side of cylindrical shaft (40) and advances from first end (42) toward the second end (44) of cylindrical shaft (40).

Arcuate side (82) of blade (80) is connected with second side (44) of cylindrical shaft (40). Arcuate side (82) of blade (80) is of a dimension wider than the diameter of cylindrical shaft (40). Arcuate side (82) is also provided with first wing (84) and second wing (86) where each wing (84, 86) extends away from the longitudinal axis of cylindrical shaft (40). As shown in FIGS. 1 and 2, each wing (84, 86) is arched away from first end (42) of cylindrical shaft (40).

Straight side (90) of blade (80) is of lesser length than arcuate side (82) and positioned opposite from arcuate side (82). Straight side (90) includes first end (92) and second end (94). First converging edge (96) connected to first wing (84) and second converging edge (98) connected second wing (86) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial or osteogenic substances into the surgically created cavity.

Figure 5:
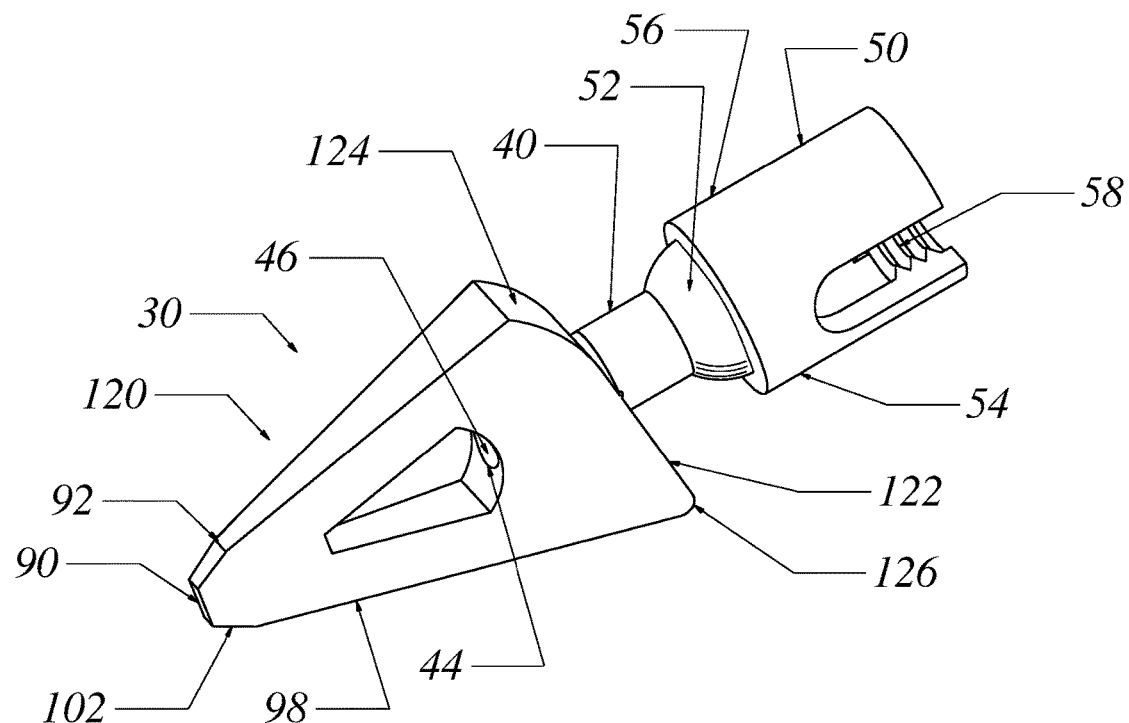
FIG. 5 is a perspective of a third preferred embodiment of the implant.
Figure 6:
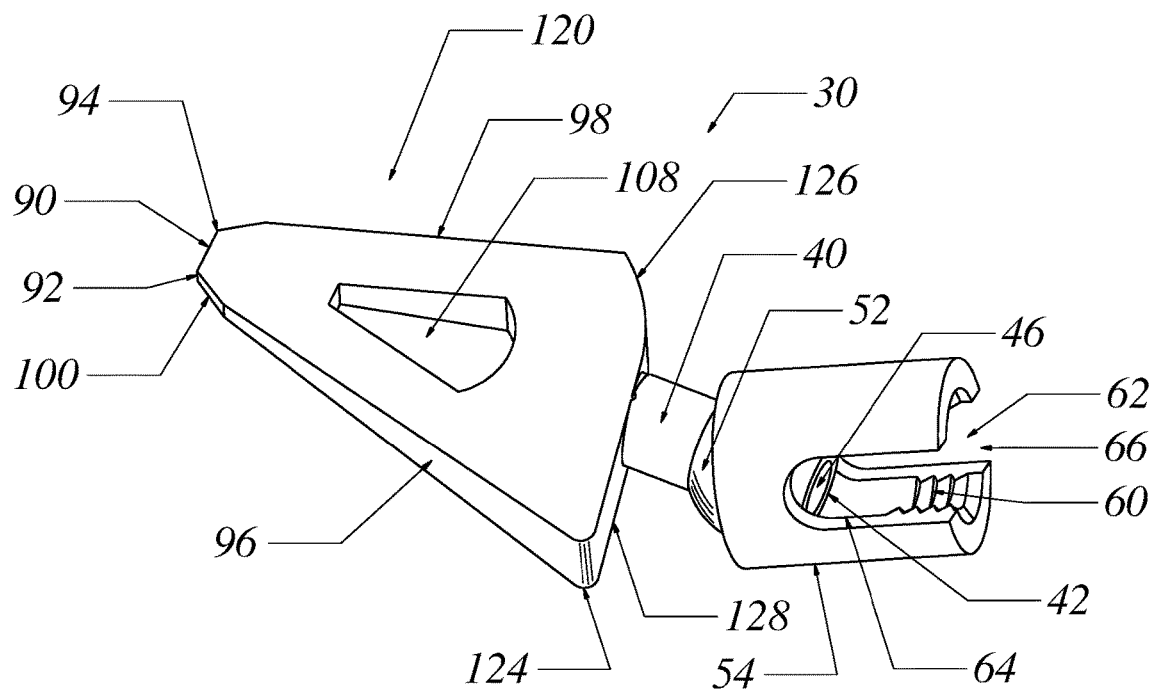
FIG. 6 is a perspective of a third preferred embodiment of the implant.

FIGS. 5 and 6 are perspectives of a third preferred embodiment of implant (30). Within the scope of the current invention, implant (30) can be interconnected with a device distinct from the implant. It has been discovered that implant (30) is useful for spinal surgeries, and, in particular, surgeries for the cervical region of the spine.

Among other things, the preferred embodiment of implant (30), enabled in FIGS. 5 and 6, includes cylindrical shaft (40), polyaxial head (50) and blade (120). Cylindrical shaft (40) includes first end (42), second end (44) and inner cavity (46) extending through first end (42) and second end (44).

Polyaxial head (50) of implant (30) is adapted for connection with a device (not shown) distinct from implant (30). Examples of devices connectable to polyaxial head (50) include but are not limited to: rods, cross-links, bars, screws, and locking nuts. Polyaxial head (50) is provided with spheroid (52) connected to first end (42) of cylindrical shaft (40) and socket (54) connected to spheroid (52). Prior to surgical fixation, the combination of spheroid (52) and socket (54) allows polyaxial head (50) to be moved in a multitude of axes relative to the longitudinal axis or inner cavity (46) of cylindrical shaft (40). Socket (54) is provided with an outward housing (56) and inward receptacle (58) including one or more threads (60). Selected preferred embodiments of housing (56) can be provided with openings (62, 64, 66) adapted to receive one or more devices distinct from implant (30).

Slanted side (122) of blade (120) is connected with second side (44) of cylindrical shaft (40). Slanted side (122) of blade (120) is of a dimension wider than the diameter of cylindrical shaft (40). Slanted side (122) includes first wing (124) and second wing (126) where each wing (124, 126) extends away from the longitudinal axis of cylindrical shaft (40). As shown in FIGS. 5 and 6, a first one of the wings (124, 126) is arcuate and arched away from the first end cylindrical shaft (40). A second one of the wings (124, 126) is provided with a pitched plane (128) facing first end (42) of cylindrical shaft (40). The combination of an arcuate wing and a wing including a pitched plane creates an asymmetric blade (120). Pitched plane (128) intersects the longitudinal axis of implant (30) at an angle of between five and eighty five degrees as measured from the distal point of pitched plane (128) to the intersection of pitched plane and implant's (30) longitudinal axis.

Straight side (90) of blade (120) is of lesser length than slanted side (122) and positioned opposite from slanted side (122). Straight side (90) includes first end (92) and second end (94). First converging edge (96) connected to first wing (124) and second converging edge (98) connected second wing (126) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial or osteogenic substances into the surgically created cavity.

Figure 7:
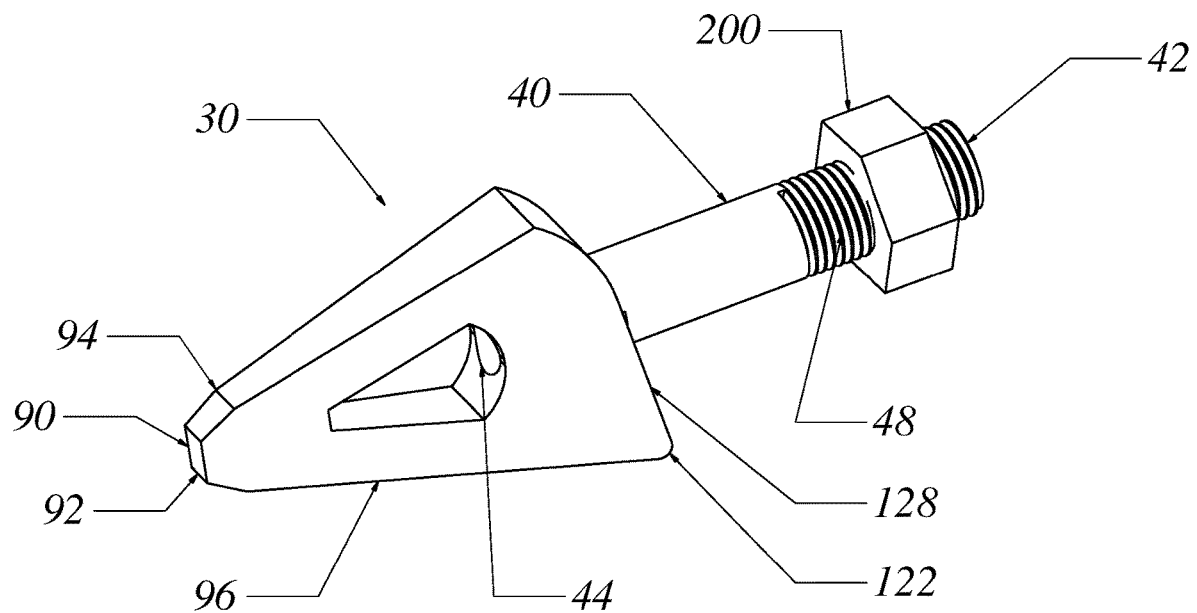
FIG. 7 is a perspective of a fourth preferred embodiment of the implant.
Figure 8:
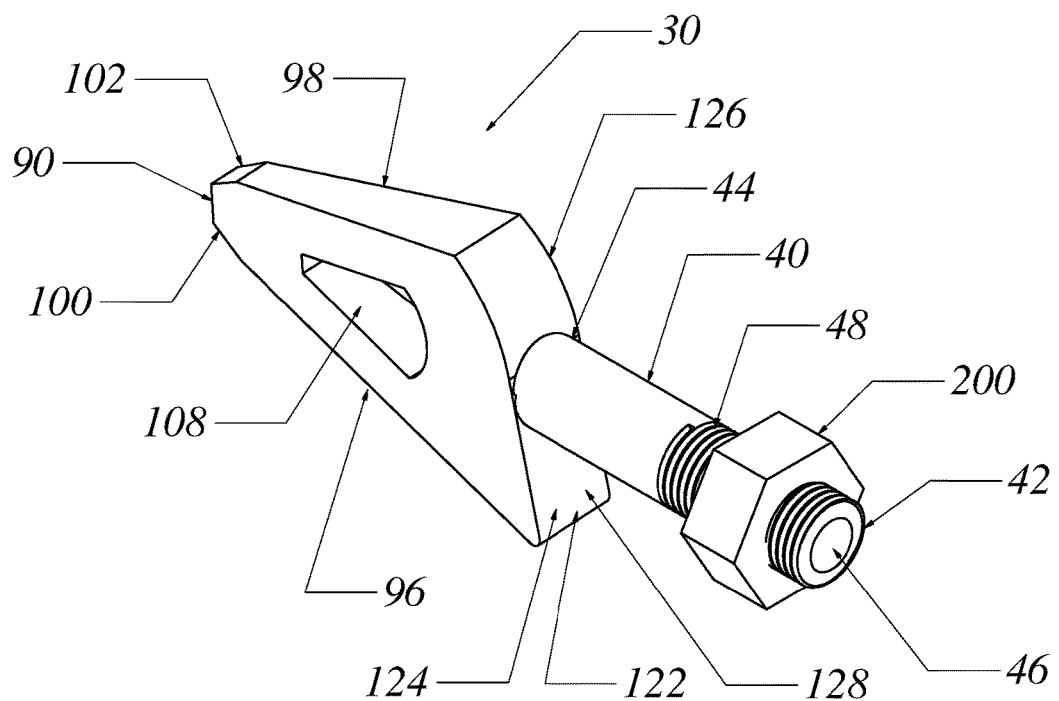
FIG. 8 is a perspective of a fourth preferred embodiment of the implant.

FIGS. 7 and 8 are perspectives of a fourth preferred embodiment of implant (30). Within the scope of the current invention, implant (30) can be interconnected with a device distinct from the implant, such as a nut (200) or other device (not shown) for coupling with implant (30). It has been discovered that implant (30) is useful for spinal surgeries, and, in particular, surgeries for the cervical region of the spine.

Among other things, the preferred embodiment of implant (30), enabled in FIGS. 7 and 8, includes cylindrical shaft (40) and blade (120). Cylindrical shaft (40) includes first end (42), second end (44) and inner cavity (46) extending through first end (42) and second end (44). First end (42) of cylindrical shaft (40) is provided with thread (48) that can be utilized to connect implant (30) to a device distinct from implant (30). Thread (48) runs about at least a portion of the outward side of cylindrical shaft (40) and advances from first end (42) toward the second end (44) of cylindrical shaft (40).

Slanted side (122) of blade (120) is connected with second side (44) of cylindrical shaft (40). Slanted side (122) of blade (120) is of a dimension wider than the diameter of cylindrical shaft (40). Slanted side (122) includes first wing (124) and second wing (126) where each wing (124, 126) extends away from the longitudinal axis of cylindrical shaft (40). As shown in FIGS. 7 and 8, a first one of the wings (124, 126) is arcuate and arched away from the first end cylindrical shaft (40). A second one of the wings (124, 126) is provided with a pitched plane (128) facing first end (42) of cylindrical shaft (40). The combination of an arcuate wing and a wing including a pitched plane creates an asymmetric blade (120). Pitched plane (128) intersects the longitudinal axis of implant (30) at an angle of between five and eighty five degrees as measured from the distal point of pitched plane (128) to the intersection of pitched plane and implant's (30) longitudinal axis.

Straight side (90) of blade (120) is of lesser length than slanted side (122) and positioned opposite from slanted side (122). Straight side (90) includes first end (92) and second end (94). First converging edge (96) connected to first wing (124) and second converging edge (98) connected second wing (126) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial or osteogenic substances into the surgically created cavity.

Within the scope of the current present invention, select preferred embodiments can be provided with a surgical wedge cutter (250) and a permanent shaft (240) or a releasable shaft (240).

FIGS. 9-12 portray a fifth and sixth embodiments of the current invention.

Figure 9:
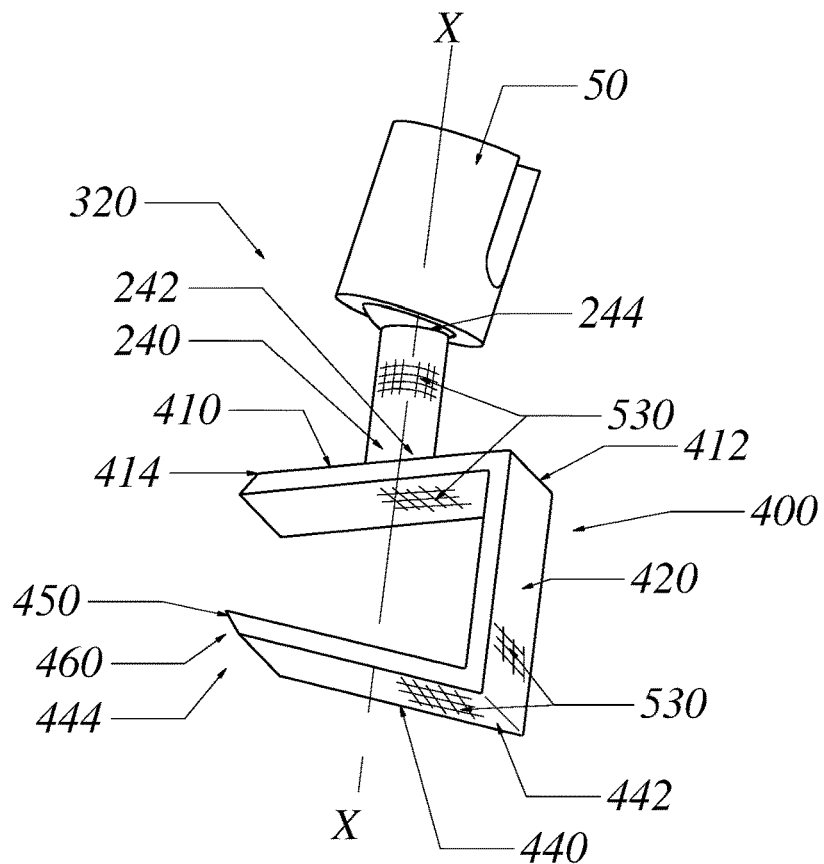
FIG. 9 is a perspective of a fifth preferred embodiment of the implant.
Figure 10:
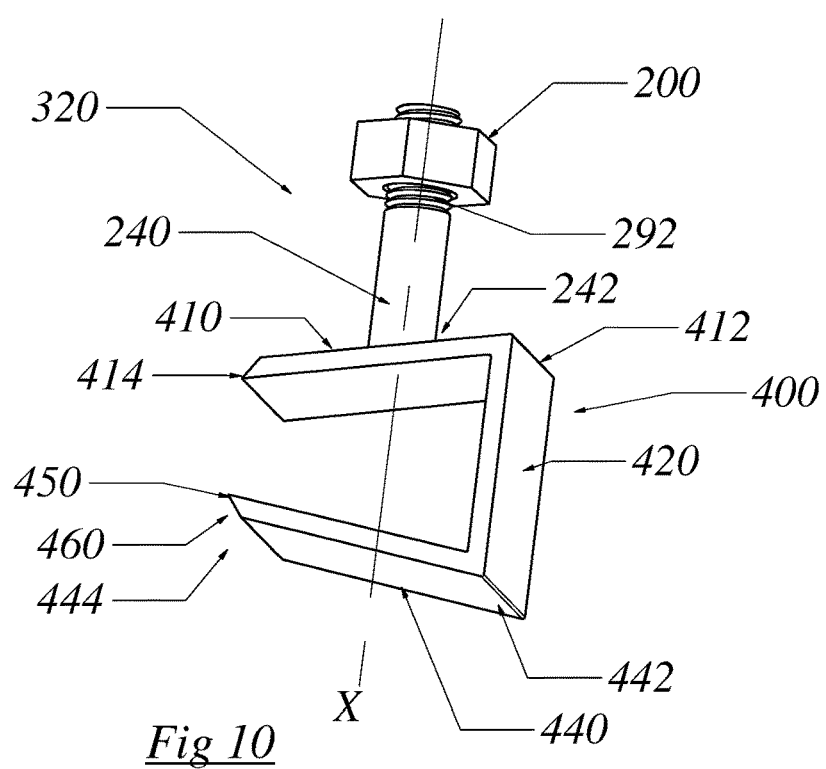
FIG. 10 is a perspective of a fifth preferred embodiment of the implant.

FIGS. 9-10 enable an implant (320) for bone adapted for interconnection with a device distinct from the implant (320). Select embodiments of implant (320) include surface treatments (530) in anticipation of improving attachment of bone to implant (320).

Head (50) (also shown in FIGS. 1-2 and 5-6) of implant (320) is adapted for connection with a device (not shown) distinct from implant (320). Head (50) is connected to second end (244) of shaft (240). Depending on engineering parameters, head (50) can be fixed, uniaxial or polyaxial. Examples of devices connectable to head (50) include but are not limited to: rods, bars, cross-links, screws and locking nuts. In other preferred embodiments of implant (320), instead of head (50), second end (244) of shaft (240) can be provided with thread (292).

First arm (410) of clip (400) is connected to first end (242) of shaft (240). In select preferred embodiments, first arm (410) is adapted to range from perpendicular to oblique with respect to the longitudinal axis (X-X) of shaft (240). Bridge (420) of clip (400) connects first end (412) of first arm (410) to first end (442) of second arm (440) of clip (400). When clip (400) is used, second arm (440) is adapted to range from perpendicular to oblique with respect to the longitudinal axis (X-X) of shaft (240) and second end (414) of first arm (410) and second end (444) of second arm (440) are biased toward each other.

Blade (450) can be positioned proximate the second end (444) of the second arm (440). Select embodiments of blade (450) can include bevel (460). Within the scope of the current implant (320), blade (450) is adapted to cut in a forward direction, i.e, away from the surgeon.

Bridge (420) can be utilized to bias the second end (414) of first arm (410) toward the second end (444) of the second arm (440). First arm (410), second arm (440) are manufactured from materials acceptable in the art. In other embodiments, clip's (400) first arm (410), second arm (440) and bridge (420) can create a spring (400).

Clip (400) of implant (320) is configured to clip bone. It is believed that clip (400) is particularly useful in clipping an occiput or part of the posterior cervical spine. Preferred embodiments of implant (320) are manufactured of titanium alloys, stainless steel, non-resorbable polymers or any other composition acceptable in the art.

Figure 11:
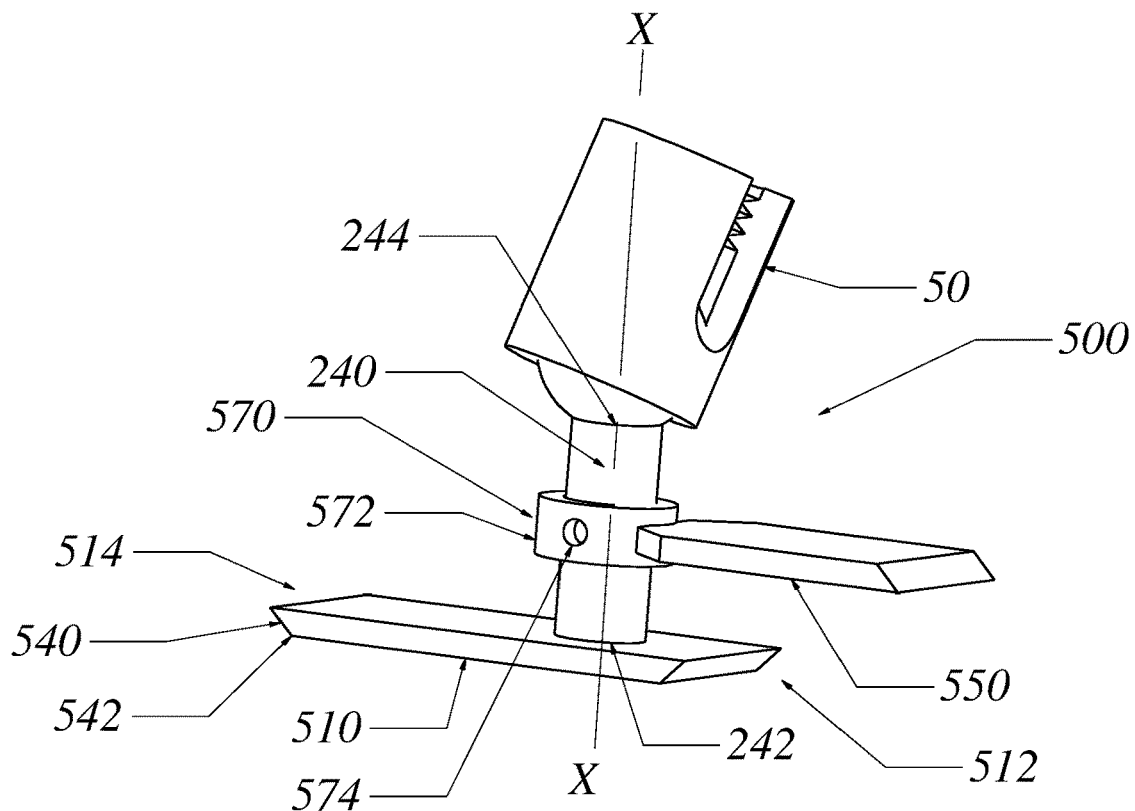
FIG. 11 is a perspective of a sixth preferred embodiment of the implant.
Figure 12:
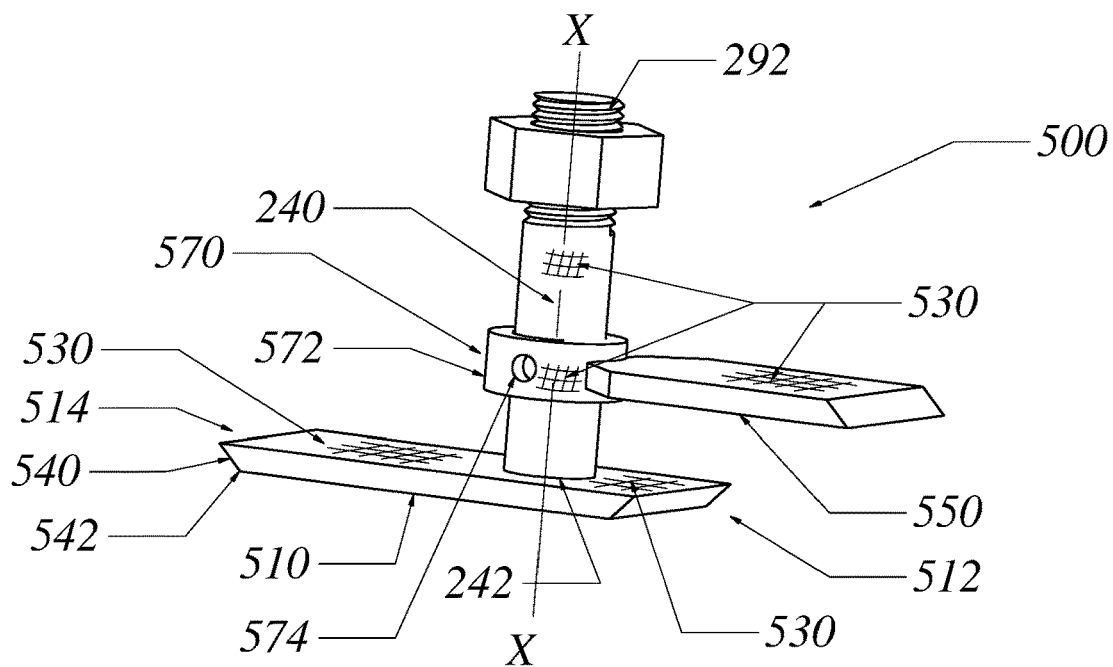
FIG. 12 is a perspective of a sixth preferred embodiment of the implant.

FIGS. 11-12 enable an implant (500) for bone adapted for interconnection with a device distinct from the implant (500). Select embodiments of implant (500) include surface treatments (530) in anticipation of improving attachment of bone to implant (500).

Head (50) (also shown in FIGS. 1-2 and 5-6) of implant (500) is adapted for connection with a device (not shown) distinct from implant (500). Head (50) is connected to second end (244) of shaft (240). Depending on engineering parameters, head (50) can be fixed, uniaxial or polyaxial. Examples of devices connectable to head (50) include but are not limited to: rods, bars, cross-links, screws and locking nuts. In other preferred embodiments of implant (500), instead of head (50), second end (244) of shaft (240) can be provided with thread (292).

Shaft (240) is provided with first end (242) and a second end (244) opposite the first end (242). Shaft (240) includes longitudinal axis (X-X). First end (242) of shaft (240) is attached proximate first end (512) of cutting member (510). Second end (514) of cutting member (510) is opposite from first end (512). Blade (540) is positioned proximate the second end (514) of cutting member (510). In select preferred embodiments, blade (540) includes bevel (542). Within the scope of the current implant (500), blade (510) is adapted to cut in a forward direction, i.e, away from the surgeon.

Appendage (550) of implant (500) is positioned about shaft (240) and between first end (242) and second end (244) of the shaft (240). In select preferred embodiments, appendage (550) is parallel to cutting member (510). Connector (570) is connected to shaft (240) and appendage (550) allowing appendage (550) to rotate about shaft (240) at angles perpendicular to the longitudinal axis (X-X) of shaft (240). In select preferred embodiments of implant (500), the connector (570) can be a collar (570). As shown, lock (572) can prevent rotation of appendage (550). Lock (572) can include receptacle (574) extending through collar (570). Receptacle (574) is adapted to receive a screw distinct from implant (570). Preferred embodiments of implant (500) are manufactured of titanium alloys, stainless steel, non-resorbable polymers or any other composition acceptable in the art.

Applicant has enabled, described and disclosed the invention as required by the Patent Cooperation Treaty and Title 35 of the United States Code.

What is claimed is:

1. An implant for bone adapted for interconnection with a device distinct from the implant; the implant comprising:
    a) a shaft comprising a first end and a second end opposite the first end; the shaft including a longitudinal axis (X-X) therein and extending away from the first end and the second end; and
    b) a clip integral with the shaft; the clip comprising:
        i) a first arm connected to first end of shaft; the first arm adapted to range from perpendicular to oblique with respect to the longitudinal axis (X-X);
        ii) a linear bridge connecting a first end of the first arm to a first end of a second arm; the second arm adapted to range from perpendicular to oblique with respect to the longitudinal axis (X-X), wherein a second end of first arm and a second end of the second arm are biased toward each other; and
        iii) a blade positioned proximate the second end of the second arm.

2. The implant of claim 1, wherein the blade is adapted to cut in a forward direction.

3. The implant of claim 2, wherein the bridge biases the second end of first arm toward the second end of the second arm.

4. The implant of claim 3, wherein the clip is configured to clip bone.

5. The implant of claim 4, wherein the bone is part of an occiput or part of the posterior cervical spine.

6. The implant of claim 3, wherein blade comprises a bevel.

7. The implant of claim 3 comprising a head connected to the second end of the shaft.

8. The implant of claim 7, wherein the head is a polyaxial head.

9. The implant of claim 3, wherein the second end of shaft comprises a thread.

10. The implant of claim 3 comprising surface treatments.

11. An implant for bone adapted for interconnection with a device distinct from the implant; the implant comprising:
   a) a shaft comprising a first end and a second end opposite the first end; the shaft including a longitudinal axis (X-X);
   b) the first end of the shaft attached proximate a first end of a cutting member;
   c) a second end of the cutting member opposite from the first end and a blade positioned proximate the second end of the cutting member;
   d) an appendage positioned about the shaft and between the first end and the second end of the shaft; the appendage parallel to the cutting member;
   e) a connector, positioned at a first end of the appendage, connected to the shaft and the appendage; the appendage extending perpendicularly in a single direction away from the longitudinal axis such that the appendage is rotatable about the shaft at angles perpendicular to the longitudinal axis (X-X); and
   f) a lock preventing rotation of the appendage.

12. The implant of claim 11, wherein the blade is adapted to cut in a forward direction.

13. The implant of claim 12, wherein the connector is a collar.

14. The implant of claim 13, wherein the lock comprises a receptacle extending through the collar; the receptacle adapted to receive a screw distinct from the implant.

15. The implant of claim 13, wherein blade comprises a bevel.

16. The implant of claim 13 comprising a head connected to the second end of the shaft.

17. The implant of claim 16, wherein the head is a polyaxial head.

18. The implant of claim 13, wherein the second end of shaft comprises a thread.

19. The implant of claim 13 comprising surface treatments.

* * * * *